(12) United States Patent
Imai et al.

(10) Patent No.: US 9,981,114 B2
(45) Date of Patent: May 29, 2018

(54) WINGED INJECTION NEEDLE

(71) Applicant: FORCE ENGINEERING CO., LTD., Utsunomiya-shi, Tochigi (JP)

(72) Inventors: Takanori Imai, Utsunomiya (JP); Hiroshi Hirota, Nasushiobara (JP)

(73) Assignee: FORCE ENGINEERING CO., LTD., Utsunomiya-shi (JP)

( * ) Notice: Subject to any disclaimer, the term of this patent is extended or adjusted under 35 U.S.C. 154(b) by 76 days.

(21) Appl. No.: 15/022,822

(22) PCT Filed: Dec. 15, 2014

(86) PCT No.: PCT/JP2014/083091
§ 371 (c)(1),
(2) Date: Mar. 17, 2016

(87) PCT Pub. No.: WO2015/111324
PCT Pub. Date: Jul. 30, 2015

(65) Prior Publication Data
US 2016/0228672 A1 Aug. 11, 2016

(30) Foreign Application Priority Data

Jan. 21, 2014 (JP) .................................. 2014-008278

(51) Int. Cl.
*A61M 5/32* (2006.01)
*A61M 25/06* (2006.01)
(Continued)

(52) U.S. Cl.
CPC ...... *A61M 25/0612* (2013.01); *A61M 5/3257* (2013.01); *A61M 5/3275* (2013.01);
(Continued)

(58) Field of Classification Search
CPC ........ A61M 5/3275; A61M 2005/3268; A61M 25/0612; A61M 5/3257
See application file for complete search history.

(56) References Cited

U.S. PATENT DOCUMENTS

| 4,735,618 A | 4/1988 | Hagen | |
| 5,512,050 A * | 4/1996 | Caizza | A61M 5/3275 604/198 |

(Continued)

FOREIGN PATENT DOCUMENTS

| JP | H10-305101 A | 11/1998 |
| JP | 2003-164525 A | 6/2003 |

(Continued)

OTHER PUBLICATIONS

Feb. 10, 2015 International Search Report issued in International Patent Application No. PCT/JP2014/083091.

*Primary Examiner* — Bhisma Mehta
*Assistant Examiner* — Benjamin Koo
(74) *Attorney, Agent, or Firm* — Oliff PLC

(57) ABSTRACT

A winged injection needle including an injection needle main body, a base that supports the base end of the injection needle main body and wings that protrude from the base toward the left and right sides to function as handles, the wings being constructed with plate members that are freely foldable through hinge sections so that in the folded state, they protrude from the base toward the left and right sides to function as handles, while in the expanded state, they extend from the base along the injection needle main body toward the leading edge of the injection needle to function as a safety cover that covers the injection needle main body.

4 Claims, 2 Drawing Sheets

(51) Int. Cl.
    *A61M 5/158*         (2006.01)
    *A61M 19/00*        (2006.01)
    *A61B 17/34*        (2006.01)

(52) U.S. Cl.
    CPC .......... *A61B 17/3401* (2013.01); *A61M 5/158* (2013.01); *A61M 19/00* (2013.01); *A61M 2005/325* (2013.01); *A61M 2005/3268* (2013.01)

(56) References Cited

U.S. PATENT DOCUMENTS

| | | |
|---|---|---|
| 7,211,069 B2 | 5/2007 | Lehmann |
| 2003/0181871 A1 | 9/2003 | Wilkinson et al. |

FOREIGN PATENT DOCUMENTS

| | | |
|---|---|---|
| JP | 2003-310756 A | 11/2003 |
| WO | 2013/016365 A2 | 1/2013 |

\* cited by examiner

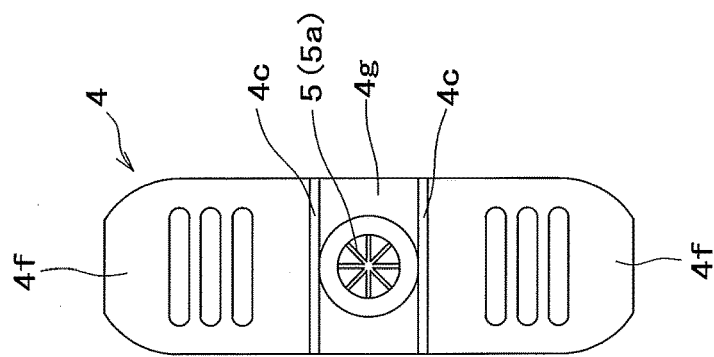
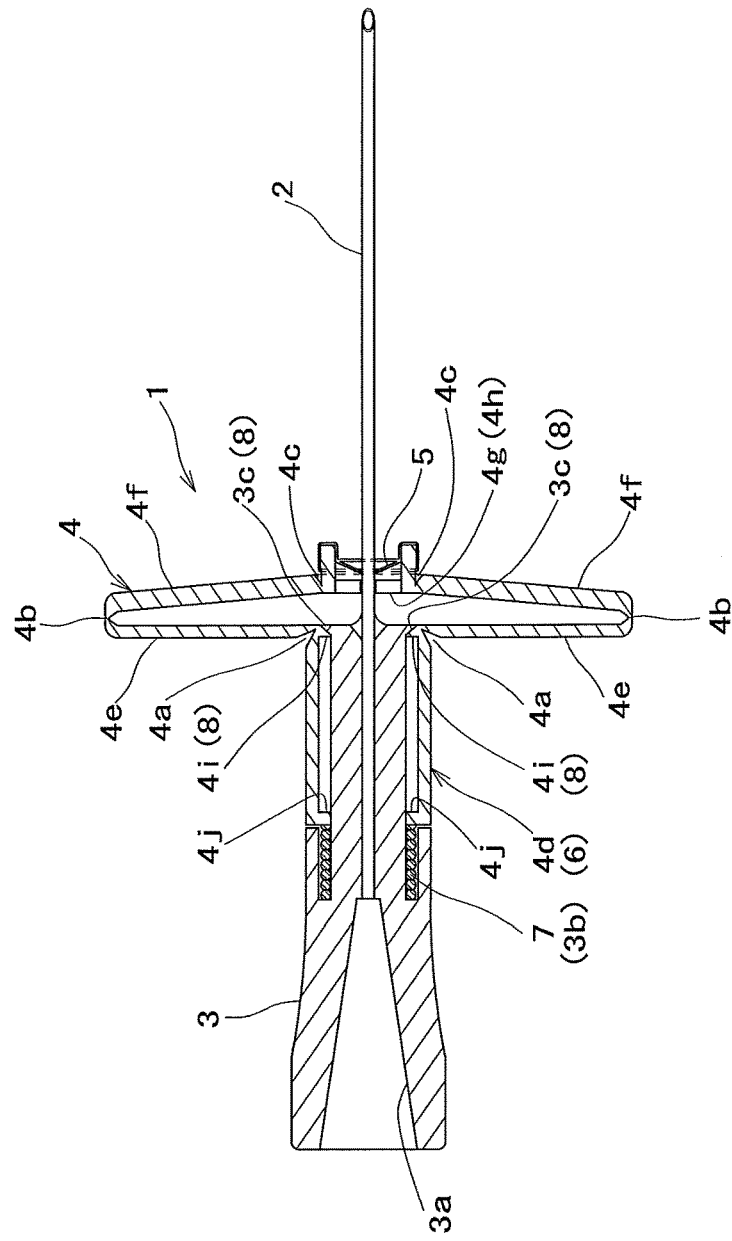
Fig. 1 (B)
Fig. 1 (A)

WINGED INJECTION NEEDLE

This is a National Phase of International Patent Application No. PCT/JP2014/083091 filed Dec. 15, 2014, which claims the benefit of Japanese Patent Application No. 2014-008278 filed Jan. 21, 2014.

TECHNICAL FIELD

The present invention relates to the technical field of a winged injection needle device to be used for epidural anesthesia and the like.

BACKGROUND ART

Winged injection needle devices for use in epidural anesthesia and the like are known (see Patent Literature 1, for example). Such winged injection needle devices have a construction comprising an injection needle, a base member which supports the base end of the injection needle, and wings which protrude from the base member toward the left and right sides, the left and right wings functioning as a handle during use, allowing piercing to be accomplished in a stable manner.

Incidentally, when a used injection needle device is discarded as is, there is a risk that the needle tip may pierce the human body while being treated as waste, resulting in problems such as infection. Therefore, after use, it is encouraged to dispose of an injection needle device after covering it with a sheath-like safety cover (cap). However, with injection needle devices used for epidural anesthesia and the like, which have longer lengths for their injection needles compared to ordinary injection needle devices, there is a risk of inadvertent piercing of a finger by the injection needle when a medical attendant (doctor, nurse, etc.) covers the leading edge of the injection needle with a sheath-like safety cover.

To deal with this problem, there have been proposed safety covers composed of a tube-like body (nested or bellows-like type) that is freely expandable in the lengthwise direction of the injection needle, with a cover formed at one end thereof, and the other end being mounted on the base member of the injection needle device (see Patent Literature 2, for example). Such safety covers allow the injection needle to be covered by a maneuver of stretching from the base side of the injection needle, thus eliminating the problem of inadvertently piercing the finger with the injection needle when covering the injection needle.

CITATION LIST

Patent Literature

[Patent Literature 1] Japanese Published Unexamined Patent Application No. 1110-305101
[Patent Literature 2] Japanese Published Unexamined Patent Application No. 2003-164525

SUMMARY OF INVENTION

Technical Problem

However, when a safety cover as described in Patent Literature 2 has been provided in a winged injection needle device, not only does a structure of the base member of the injection needle become complex, but the safety cover becomes a hindrance when the wings are used as handles, or conversely, the wings become a hindrance when the safety cover is stretched.

Solution to Problem

In light of this situation, the present invention has been devised with the aim of solving these problems, and therefore the invention of claim 1 is a winged injection needle comprising an injection needle main body, a base that supports the base end of the injection needle main body, and wings protruding from the base toward the left and right sides, functioning as handles, the wings being constructed with plate members that are freely foldable through hinge sections, so that in the folded state, the wings protrude from the base toward the left and right sides to function as handles, while in the expanded state, the wings extend along the injection needle main body from the base toward the leading edge of the injection needle to function as a safety cover covering the injection needle main body, and injection needle retraction means which causes the injection needle main body to retract from the wings during the procedure of expanding the wings, the wings each comprising a cylinder that fits around the base, a first plate section connected to a front end of the cylinder in a freely foldable manner through a first hinge section, a second plate section connected to a tip of the first plate section in a freely foldable manner through a second hinge section, and a tip plate section connected to a tip of the second plate section in a freely foldable manner through a third hinge section, and by valley folding the first hinge sections, mountain folding the second hinge sections and valley folding the third hinge sections, the wings protrude from the base toward the left and right sides with the first plate sections and the second plate sections in a front/back overlapping folded state, to function as handles, while in the expanded state with all of the hinge sections expanded in a linear manner, the first plate sections and second plate sections extend along the injection needle main body from the base toward the leading edge of the injection needle to function as the safety cover covering the injection needle main body, the injection needle retraction means comprising a slide supporting member that supports the base in a freely slidable manner in the direction of retraction by the cylinder of the wings, a spring that energizes the base in the direction of retraction, and an engagement section that engages with and holds the base in a non-rear position, the base and the injection needle main body being forced to retract with respect to the cylinder of the wings in response to release of engagement by the engagement section.

Advantageous Effects of Invention

According to the invention of claim 1, since wings that originally function as handles also function as a safety cover, and therefore the structure is simpler and the number of parts are reduced, compared to providing a separate safety cover, it is possible to eliminate inconveniences such as mutual interference between operation of the wings and the safety cover.

Furthermore, the invention of claim 1 comprises injection needle retraction means that retracts the injection needle relative to the wings during the procedure of expanding the wings, thus allowing the essential length of the injection needle that is to be covered with the safety cover (wings) to be shortened, as a result making it possible to avoid enlargement of the wings due to the use of the wings as a safety cover.

Moreover, according to the invention of claim 1, the base member and injection needle are retracted by the energizing force of a spring in response to release of engagement by the engagement section, therefore eliminating the need for a maneuver for retraction of the base member and injection needle, and simplifying the procedure during use of the wings as a safety cover.

BRIEF DESCRIPTION OF DRAWINGS

FIG. 1 (A) is a plan cross-sectional view showing a winged injection needle device with the wings in the folded state, and (B) is a front view showing the wings in the folded state.

DESCRIPTION OF EMBODIMENTS

Figure 2:
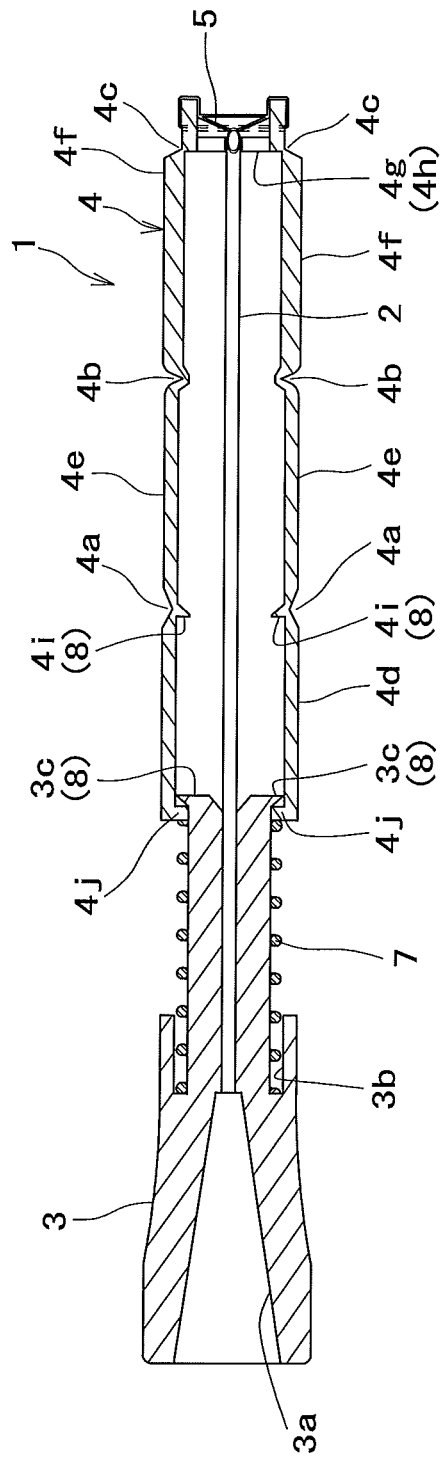
FIG. 2 is a plan cross-sectional view showing a winged injection needle device with the wings in the expanded state.

An embodiment of the present invention will now be described with reference to the accompanying drawings. In the drawings, 1 is a winged injection needle device to be used for epidural anesthesia or the like, the winged injection needle device 1 comprising an injection needle 2, a base member 3 that supports the base end of the injection needle 2, and wings 4 that protrude from the base member 3 toward the left and right sides to function as handles. At the rear end of the base member 3, there is formed a rear-tapered syringe-connecting hole 3a. By connecting a syringe (not shown) to the rear-tapered syringe-connecting hole 3a, it is possible to inject a drug in the syringe into the human body through the injection needle 2.

The left and right wings 4 are each constructed with plate members that are freely foldable through hinge sections 4a, 4b, 4c. For example, the wings 4 of this embodiment comprise a cylinder 4d that fits around the base member 3, a first plate section 4e connected to the front end of the cylinder 4d in a freely foldable manner through the first hinge section 4a, a second plate section 4f connected to the tip of the first plate section 4e in a freely foldable manner through the second hinge section 4b, and a tip plate section 4g connected to the tip of the second plate section 4f in a freely foldable manner through the third hinge section 4c.

The wings 4 constructed in this manner, when in the folded state shown in FIG. 1, protrude from the base member 3 toward the left and right sides to function as handles, while in the expanded state shown in FIG. 2, they extend from the base member 3 along the injection needle 2 toward the leading edge of the injection needle to function as a safety cover covering the injection needle 2. For example, by folding the first hinge sections 4a inward, folding the second hinge sections 4b outward and folding the third hinge sections 4c inward, the wings 4 of this embodiment protrude from the base member 3 toward the left and right sides with the first plate sections 4e and the second plate sections 4f in a front/back overlapping folded state to function as handles. When all of the hinge sections 4a, 4b, 4c are in the expanded state where they are expanded in a linear manner, the first plate sections 4e and second plate sections 4f extend from the base member 3 along the injection needle 2 toward the leading edge of the injection needle to function as a safety cover covering the injection needle 2.

The wings 4 preferably comprise return-blocking means that engages with the leading edge of the injection needle 2 to block return to the folded state when in the expanded state. For example, for this embodiment, a through-hole 4h is formed in the tip plate section 4g of the wings 4, through which the injection needle 2 runs in the folded state, and a cap 5 is provided on the through-hole 4h to function as return-blocking means. The cap 5 has a plurality of notches 5a formed in a radial fashion in an elastic thin-plate member, running through the center of the through-hole 4h. In the folded state of the wings 4, as shown in FIG. 1, elastic deformation allows penetration of the injection needle 2, while in the expanded state of the wings 4, after it clears the front of the leading edge of the injection needle 2, it engages with the leading edge of the injection needle 2 as shown in FIG. 2, to restrict return of the wings 4 to the folded state.

Furthermore, the winged injection needle device 1 of the present invention preferably comprises injection needle retraction means that retracts the injection needle 2 relative to the wings 4 during the procedure of expanding the wings 4. The purpose of this is to shorten the essential length of the injection needle 2 that is to be covered by the safety cover (wings 4) and to avoid enlargement of the wings 4. For example, the injection needle retraction means of this embodiment comprises a slide supporting member 6 that supports the base member 3 in a freely slidable manner in the direction of retraction with respect to the wings 4, a spring 7 that energizes the base member 3 in the direction of retraction, and an engagement section 8 that engages with and holds the base member 3 in the non-rear position, the construction being such that the base member 3 and injection needle 2 are retracted in response to release of engagement by the engagement section 8.

The slide supporting member 6 is constructed by supporting the front half of the base member 3 with the cylinder 4d of the wings 4 in a forward/rearward freely slidable manner. The spring 7 is housed in a compressed state in a spring-housing groove 3b of the base member 3, and energizes the cylinder 4d of the wings 4 in the forward direction, or in other words, it energizes the base member 3 in the direction of retraction with respect to the wings 4.

The engagement section 8 is constructed with an engagement nub 3c formed at the front end of the base member 3 and an engagement nub 4i formed at the front end of the cylinder 4d of the wings 4, whereby engagement between the engagement nubs 3c, 4i restricts retraction of the base member 3 with respect to the wings 4. The engagement section 8 constructed in this manner releases its engagement by outward opening of the engagement nub 4i on the wings 4 side by elastic deformation, but when the wings 4 are in the folded state, as shown in FIG. 1, the presence of the first plate section 4e that is folded outward from the engagement nub 4i causes release of engagement by the engagement section 8 to be restricted. On the other hand, when the wings 4 are expanded as shown in FIG. 2, the outward portion of the engagement nub 4i is disengaged, causing the engagement nub 4i to undergo elastic deformation so that they open outward and engagement by the engagement section 8 is automatically released. This makes it possible to cause the base member 3 and injection needle 2 to automatically retract with respect to the wings 4 during the procedure of expansion of the wings 4. Incidentally, since retraction of the base member 3 and injection needle 2 is restricted once the engagement nub 3c of the base member 3 has engaged with a rear end protrusion 4j of the cylinder 4d, the base member 3 and injection needle 2 do not fall off from the wings 4.

A method of using the winged injection needle device 1 according to the embodiment of the present invention will now be described with reference to FIG. 1 and FIG. 2.

When the winged injection needle device 1 pierces the human body, as shown in FIG. 1, the wings 4 in the folded state protruding outward from the base member 3 on the right and left sides function as handles to hold the winged injection needle device 1, and the leading edge of the injection needle 2 pierces the human body. After the human body has been pierced, operation of the syringe connected to the syringe-connecting hole 3a of the base member 3 allows a drug in the syringe to be injected into the human body through the injection needle 2.

The used winged injection needle device 1 is discarded with the injection needle 2 in a covered state. In the winged injection needle device 1 of this embodiment of the present invention, for covering of the injection needle 2, the cylinder of the wings 4 is held with one hand while the plate sections 4e, 4f of the wings 4 are pushed out forward with the other hand. The plate sections 4e, 4f that have pushed forward extend toward the leading edge of the injection needle along the injection needle 2 while being expanded, thus covering the injection needle 2. Also, when the wings 4 are expanded, engagement by the engagement section 8 is automatically released and the base member 3 and injection needle 2 retract by the energizing force of the spring 7. This causes the needle tip of the injection needle 2 to separate from the cap 5 provided at the tip of the wings 4 and thus become housed in the wings 4, while the cap 5 engages with the needle tip of the injection needle 2 and restricts return of the wings 4 to the folded state. Thus, the wings 4 reliably function as a safety cover and allow the used winged injection needle device 1 to be safely discarded.

In this embodiment constructed as described above, which is a winged injection needle device 1 comprising an injection needle 2, a base member 3 that supports the base end of the injection needle 2 and a wings 4 that protrude from the base member 3 toward the left and right sides to function as handles, the wings 4 are constructed with plate members that are freely foldable through hinge sections 4a, 4b, 4c, so that in the folded state, they protrude from the base member 3 toward the left and right sides to function as handles, while in the expanded state, they extend from the base member 3 along the injection needle 2 toward the leading edge of the injection needle to function as a safety cover that covers the injection needle 2, therefore, the structure is simpler and the number of parts are reduced, compared to providing a separate safety cover, while it is possible to eliminate inconveniences such as mutual interference between operation of the wings 4 and the safety cover.

Furthermore, since the wings 4 comprise return-blocking means (the cap 5) that engages with the leading edge of the injection needle to block return to the folded state when in the expanded state, they can reliably function as a safety cover.

Furthermore, since it comprises injection needle retraction means that retracts the injection needle 2 relative to the wings during the procedure of expanding the wings 4, it becomes possible to shorten the essential length of the injection needle 2 that is to be covered with the safety cover (wings 4), as a result making it possible to avoid enlargement of the wings 4 due to the use of the wings 4 as a safety cover.

Moreover, since the injection needle retraction means comprises a slide supporting member 6 that supports the base member 3 in a freely slidable manner in the direction of retraction with respect to the wings 4, a spring 7 that energizes the base member 3 in the direction of retraction, and an engagement section 8 that engages with and holds the base member 3 in the non-rear position, the construction being such that the base member 3 and injection needle 2 are retracted in response to release of engagement by the engagement section 8, there is no need for a maneuver to retract the base member 3 and injection needle 2, thus simplifying the procedure during use of the wings 4 as a safety cover.

Furthermore, since the engagement section 8 automatically releases its engagement in response to the procedure of expanding the wings 4, there is no need for a procedure for release of engagement of the engagement section 8, thus further simplifying the procedure during use of the wings 4 as a safety cover.

Needless to mention, the present invention is not limited to this specific embodiment above and may incorporate various modifications such as are within the scope of the claim.

INDUSTRIAL APPLICABILITY

The present invention can be utilized as a winged injection needle device for use in epidural anesthesia and the like.

DESCRIPTION OF SYMBOLS

1 Winged injection needle device
2 Injection needle
3 Base member
4 Wings
5 Cap
6 Slide supporting member
7 Spring
8 Engagement section

What is claimed is:

1. A winged injection needle device comprising:
an injection needle;
a base member that supports a base end of the injection needle, the base member including a base member engagement nub formed outside of a front end of the base member; and
wings comprising:
 a cylinder that fits around the base member, the cylinder is freely slidable relative to the base member in a direction of retraction of the injection needle,
 a first plate section connected to a front end of the cylinder in a freely foldable manner through a first hinge section,
 a second plate section connected to a tip of the first plate section in a freely foldable manner through a second hinge section,
 a tip plate section connected to a tip of the second plate section in a freely foldable manner through a third hinge section, and
 a wing engagement nub positioned on a side of the first hinge section proximate the injection needle, wherein
in a folded state, the first plate section extends from the first hinge section away from the base member by folding the first hinge section, the second plate section overlaps the first plate section by folding the second hinge, and the wing engagement nub engages the base member engagement nub,
in an expanded state, the first hinge section and the second hinge section expand in a linear manner, and the wings extend along the injection needle from the base member toward a needle tip of the injection needle to cover the injection needle, and
the wings and the base member are connected by a spring that energizes the base member in the direction of retraction, and when the engagement between the wing engagement nub and the base member engagement nub is released, the injection needle retracts with respect to the cylinder.

2. The winged injection needle device of claim 1, wherein the wings further comprise a rear end protrusion extending toward the base member from a rear end of the cylinder, opposite the wing engagement nub.

3. The winged injection needle device of claim 2, wherein a front end of the spring is attached to the rear end protrusion.

4. The winged injection needle device of claim 1, wherein the wings further comprise:
- a third plate section connected to a front end of the cylinder in a freely foldable manner through a fourth hinge section;
- a fourth plate section connected to a tip of the third plate section in a freely foldable manner through a fifth hinge section and connected to the tip plate in a freely foldable manner through a sixth hinge section; and
- a second wing engagement nub positioned on a side of the fourth hinge section proximate the injection needle, wherein in a folded state, the third plate section extends from the fourth hinge section away from the base member by folding the fourth hinge section, the fourth plate section overlaps the third plate section by folding the fifth hinge, and the second wing engagement nub engages a second base member engagement nub, the second base member engagement nub formed outside of the front end of the base member opposite the first base member engagement nub, in an expanded state, the fourth hinge section and the fifth hinge section extend in a linear manner on a side of the injection needle opposite the first hinge section and the second hinge section.

* * * * *